United States Patent [19]

Sekine et al.

[11] Patent Number: 4,715,709

[45] Date of Patent: Dec. 29, 1987

[54] SURFACE FLAW DETECTING METHOD AND APPARATUS

[75] Inventors: Yoshitada Sekine, Yoya; Fumiki Yokota, Yamato; Hisashi Kubota, Fujisawa, all of Japan

[73] Assignee: Nissan Motor Company, Limited, Yokohama, Japan

[21] Appl. No.: 727,874

[22] Filed: Apr. 26, 1985

[30] Foreign Application Priority Data

Apr. 27, 1984 [JP] Japan .................................. 59-83888
Apr. 27, 1984 [JP] Japan .................................. 59-83889
Apr. 27, 1984 [JP] Japan .................................. 59-83890

[51] Int. Cl.$^4$ ........................................... G01N 21/88
[52] U.S. Cl. .................................... 356/237; 250/563; 250/572
[58] Field of Search ............ 250/572, 234, 236, 222.1, 250/562, 563; 356/237

[56] References Cited

U.S. PATENT DOCUMENTS 4,555,727 11/1985 Nun et al. ...................... 356/237 X

FOREIGN PATENT DOCUMENTS 58-219441 12/1983 Japan .

Primary Examiner—Eugene R. LaRoche
Assistant Examiner—Robert J. Pascal
Attorney, Agent, or Firm—Schwartz, Jeffery, Schwaab, Mack, Blumenthal & Evans

[57] ABSTRACT

A method for detecting flaws in a surface of an inspected object can moderate the requirements for inspection condition accuracy, particular for adjustment of spatial relationships among a laser unit, the surface and an laser detector unit. The method includes the step of transmitting a laser beam in a known configurationonto a specular surface of the inspected object, projecting the laser beam reflected by the surface onto a light-scattering screen and forming an image of the surface on the screen, and detecting the image of the surface in the known configuration in relation to a predetermined portion of the screen. An apparatus carrying out the method includes a sensor for detecting positional deviation of the image of the surface from a fixed monitored portion of the screen, a adjuster for adjusting the angle subtended by the axes of a transmitter of the laser slit beam and a flaw-detecting image sensor and an adjuster for adjusting the inclination of a plane defined by the axes of the transmitted and the flaw-detecting image sensor relative the surface, both adjusters operating in accordance with the output of the deviation detecting sensor.

11 Claims, 28 Drawing Figures

FIG.18
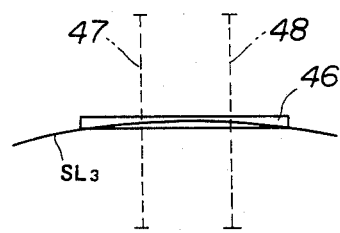
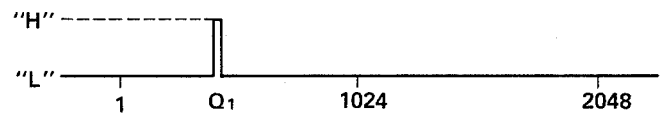
FIG.20A
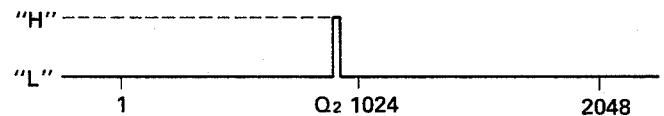
FIG.20B
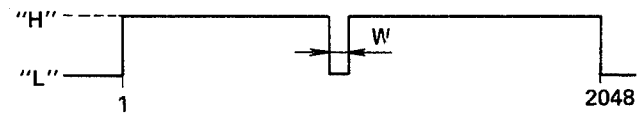
FIG.20C

SURFACE FLAW DETECTING METHOD AND APPARATUS

BACKGROUND OF THE INVENTION

1. Field of the Invention

This invention relates to a surface flaw detecting method and apparatus for inspection of specified surfaces, e.g. painted surfaces of automotive vehicle parts or specular surfaces of mechanical devices.

2. Description of the Prior Art

Recently, laser beam surface inspection in search of flaws such as small protuberances and stains has started to replace visual inspection by workers, which is less efficient and of variable quality among workers.

FIG. 1 illustrates a prior art automatic laser surface flaw detection system. This prior art surface flaw detecting system comprises a laser unit 1, and a laser detector unit 3 including a condenser lens 4 and a laser photodiode 5. The laser unit 1 transmits a laser spot beam LS onto a flat inspection surface 2. The laser photodiode 5 receives the laser spot beam specularly reflected from the inspection surface 2 through the condenser lens 4 and outputs a corresponding electrical signal.

Since laser beams are highly collimated, scattering of the laser spot beam LS from the laser unit 1 by flaws and/or small proturberances will be very conspicuous and will show up readily in the electrical output of the laser photodiode 5. Variations in the electrical output indicate flaws on the inspection surface 2.

However, this prior art automatic laser surface flaw detection system requires very accurate coincidence between the optical axes of the laser unit 1 and the condenser lens 4 in 3 dimensions on the inspection surface 2 (e.g. at a tolerance on the order of plus-minus 15' (minutes) and that this accurate 3-dimensional relationship among the laser unit 1, the inspection surface 2 and the laser detector unit 3 be maintained throughout the surface inspection operation. Thus, this method requires a surface flaw detecting apparatus with a complicated 3-dimensional positioning mechanism in order to meet the above-described conditions but even so is not suitable for methods in which a moving surface flaw detecting apparatus scans the inspection surface 2. In particular, this latter detection technique requires accurate focussing of the condenser lens 4 at every point across the inspection surface 2, so that the focus of the condenser lens 4 must be adjusted each time the inspection surface 2 moves.

Laser surface flaw detection systems employing a laser slit beam and a line sensor, e.g. consisting of CCD's and PDA, entails similar drawbacks.

This prior art automatic laser surface flaw detection technique can be applied only to flat cylindrical surfaces.

In addition, No. JP-A-58219441 discloses a convex-object-surface flaw-detecting apparatus comprising a device transmitting a beam of visible light onto a convex inspection surface of an object, a projecting screen onto which the beam of visible light is reflected by the convex inspection surface, the screen projecting a corresponding image, and an image sensor picking up the image on the screen and signalling the presence or absence of flaws in the convex inspection surface.

Since this apparatus employs collimated beam of visible light produced by a combination of a lamp and a convex lens, the reflectivity of the convex inspection surface must be rather high in order for the screen to project a clear image. In addition, this apparatus is not capable of accurate surface inspection.

SUMMARY OF THE INVENTION

An object of this invention is to provide a surface flaw detecting method by which inspection conditions, specifically the relationships among the optical axes of a laser unit, a laser detector unit and the surface of an inspected object, can be adjusted during operation, a positioning mechanism for the laser unit and the laser detector unit can be simpler and a moving surface-flaw-detecting apparatus can accurately detect surface flaws.

In order to achieve this object, a method of this invention comprises the steps of transmitting laser beams onto a reflective surface of an inspected object, projecting laser beams reflected from the surface onto a light-scattering screen so as to form an image of the surface at a fixed position on the screen, detecting the position of the image of laser beams scattered by the surface on the screen and correction of the detected position to match the fixed position.

Another object of this invention is to provide a surface flaw detecting apparatus which can obviate the need for complicated focus adjustments and handle moving surface-flaw detection. In order to achieve this invention, this inventive apparatus comprises means for transmitting laser slit beams onto a reflective surface of an inspected object, a light-scattering screen onto which the laser slit beams are reflected by the surface thus forming an image of the surface on the screen, a flaw detecting image sensor disposed in a fixed relation to the screen and capable of monitoring a predetermined portion of the screen, means, disposed in a fixed relation of the screen, for detecting the disposition of the image of the surface relative to the predetermined portion of the screen, means for adjusting the angular displacement between the axes of said laser slit beams transmitting means and the flaw detecting image sensor in accordance with the output of said position detecting means, and means for adjusting the inclination of the plane of the incident and reflected laser slit beam relative to the surface in response to the output of said position detecting means.

BRIEF DESCRIPTION OF THE INVENTION

FIG. 18 is a diagram showing the disposition of the slit image within a monitored reference strip on the screen 13;

Figure 19:
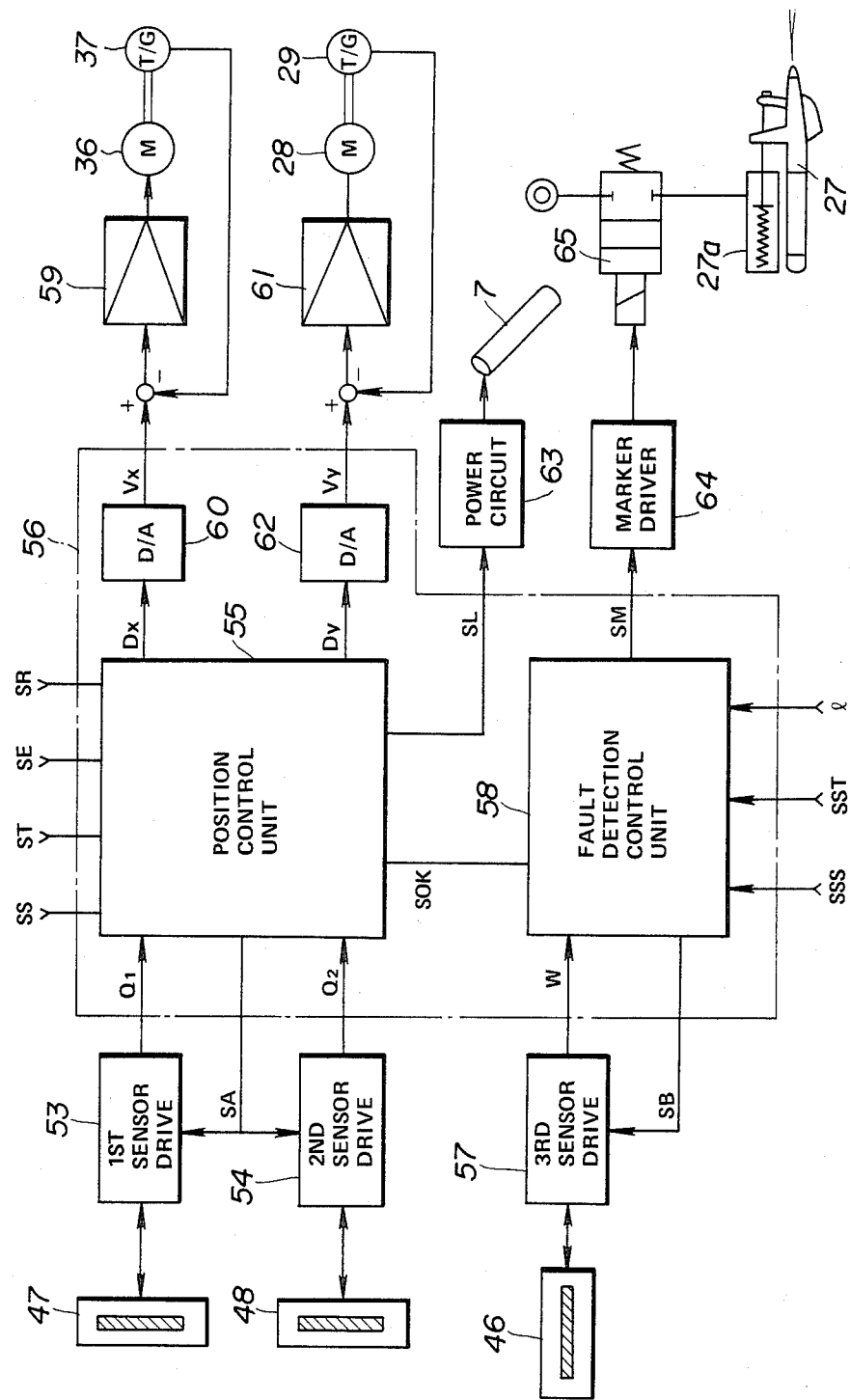
FIG. 19 is a block diagram of a control system of the laser surface flaw detecting apparatus of FIG. 7.
Figure 21:
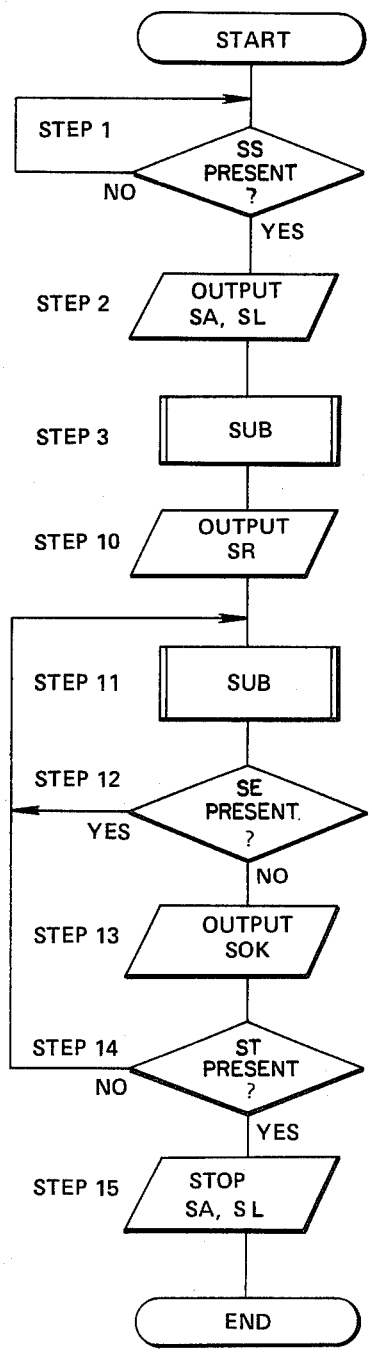
Figure 22:
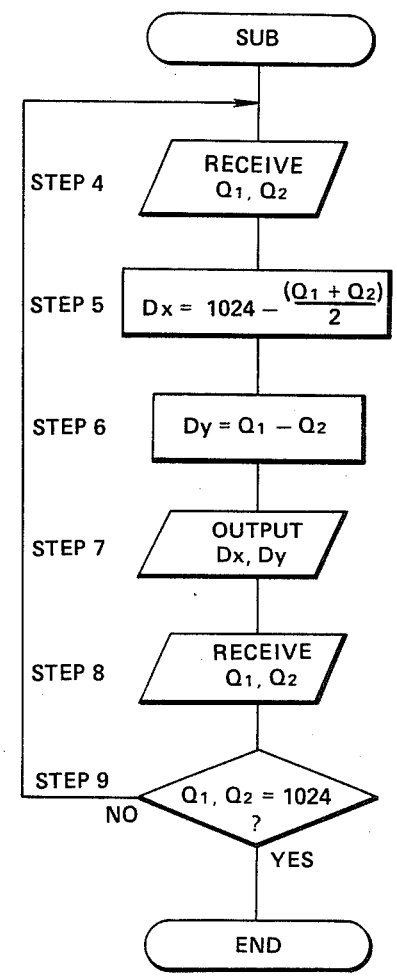
Figure 23:
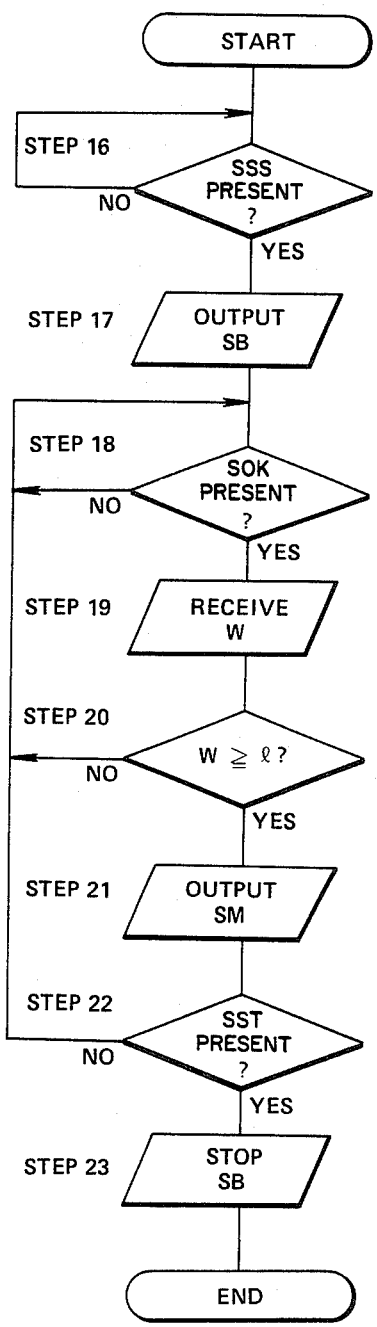
Figure 24:
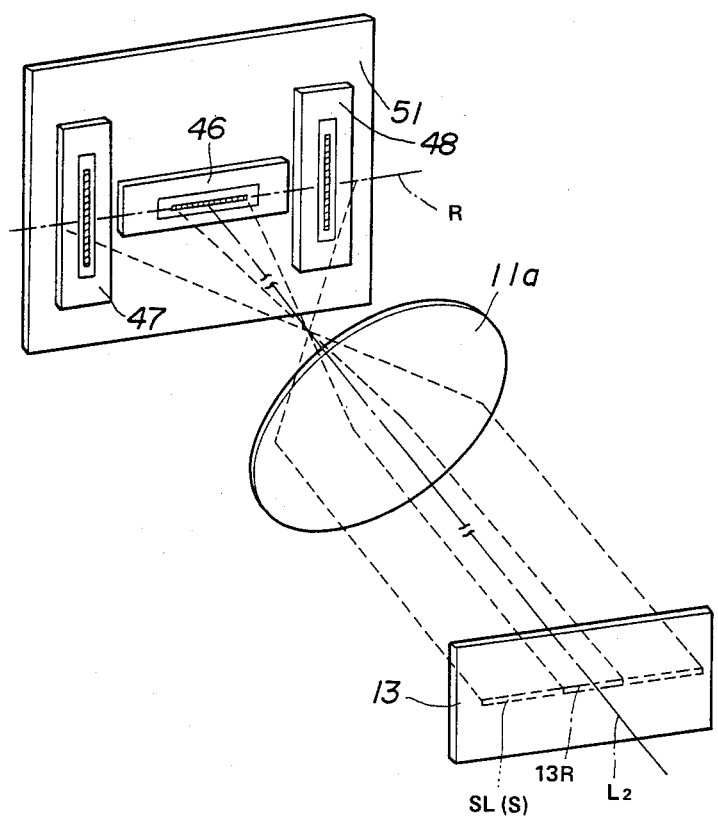
Figure 25:
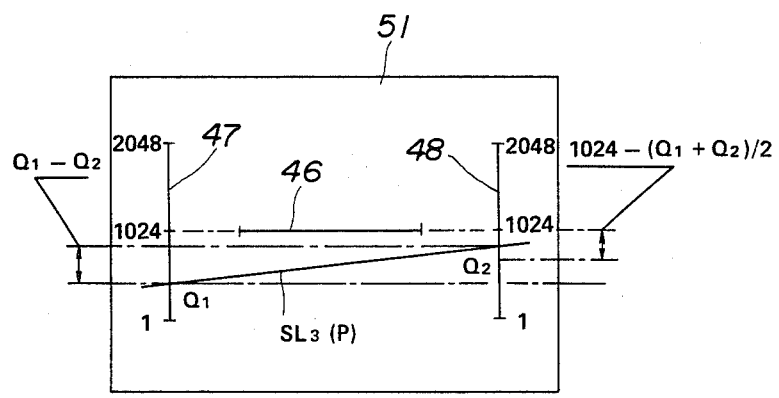

FIGS. 20 A–C are a timing chart of the outputs of first, second and third sensor drive circuits;

FIG. 21 is a main program flowchart of a position control unit shown in FIG. 19;

FIG. 22 is a subroutine flowchart of the position control unit shown in FIG. 19;

FIG. 23 is a program flowchart of a laser surface flaw detection control unit shown in FIG. 19;

FIG. 24 is a perspective illustration of the interior of a laser detector unit according to a third embodiment of this invention; and FIG. 25 is a diagram showing how the position of a slit image is detected by position detecting line sensors according to the third embodiment of this invention.

DESCRIPTION OF THE PREFERRED EMBODIMENTS

The preferred embodiments of this invention will be described in detail with reference to FIGS. 2 to 25.

FIRST EMBODIMENT

A laser surface flaw detecting apparatus according to a first embodiment of this invention comprises a support beam 6 with a mount disc 6a for attachment to a fixed or moving device (not shown), a laser unit 7 mounted at one end of the support beam 6, and a laser detector unit 8 mounted at the other end of the support beam 6. The angle between the optical axes $L_1$ of the laser unit 7 and the optical axis $L_2$ of the laser detector unit 8 is labelled $\delta$. The respective optical axes $L_1$ and $L_2$ of the laser unit 7 and the laser detector unit 8 are each inclined at an angle of $\delta/2$ to a plane 9 normal to the inspected surface 10 which is a nearly specular surface, e.g. a painted outer surface of an automotive vehicle door.

The laser unit 7 includes, for example, a He-Ne laser (not shown) and a lens system 7a ending in a slit (not shown) capable of converting the laser beam from the He-Ne laser into laser slit beams LST. The slit widens in the direction of propagation. Alternatively, the laser beam may be a spot beam scanned back and forth to simulate a time-constant slit by a rotating polygonal mirror.

The laser detector unit 8 includes a camera 11 and an opaque cylinder 12. The camera 11 includes a condenser lens 11a and a line sensor 11b composed of an array of photoelectric sensors, e.g. CCD's. The opaque cylinder 12 is mounted on the front of the camera 11 and has a light-transmissive projection screen 13 at its lower end.

The line sensor 11b is fixed to a predetermined location within the camera 11 in order to continuously monitor a fixed reference strip on the screen 13 onto which the laser slit beams LST from the laser unit 7, reflected by the inspected surface 10 are expected to fall.

The screen 13 lies in the one focal plane of the condenser lens 11a. The screen 13 is made of light-scattering material, e.g. a frosted glass or matte plate commonly used as a focal plate in cameras. It is best to use a completely light-scattering material.

Figure 1:
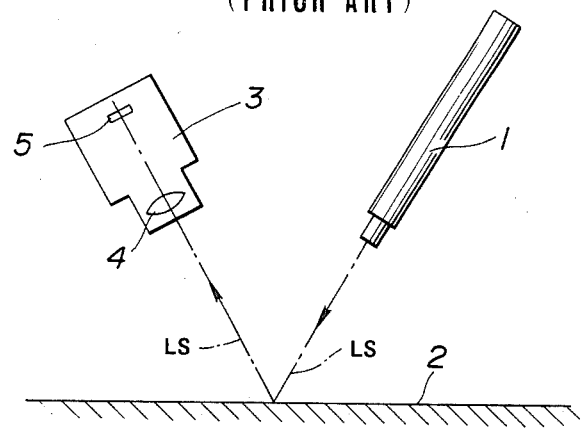
FIG. 1 is a schematic diagram of a prior art laser surface flaw detecting system.
Figure 2:
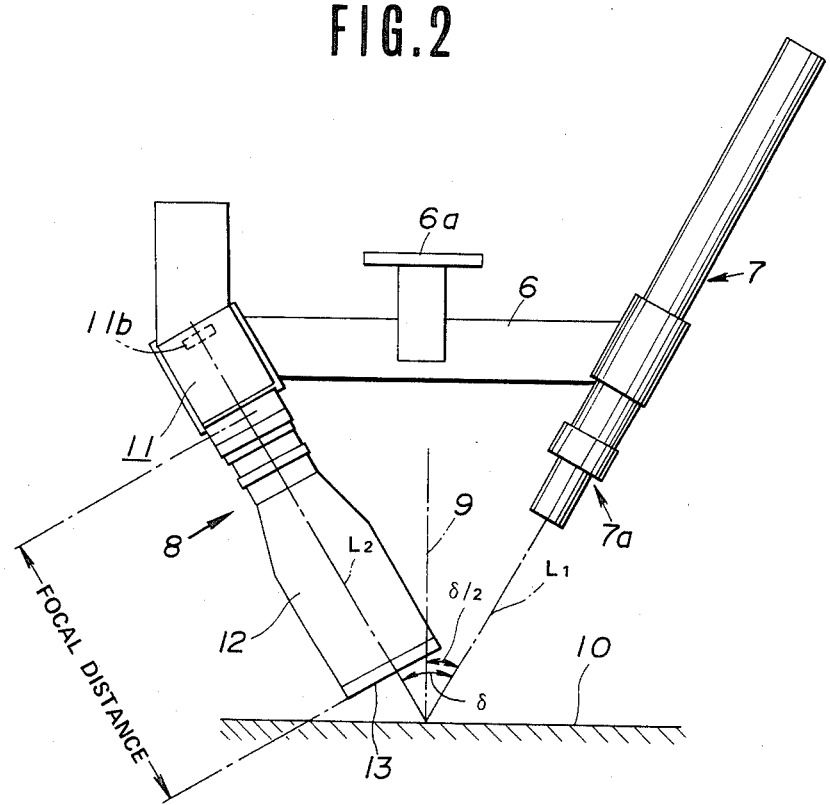
FIG. 2 is a front elevation of a laser surface flaw detecting apparatus according to a first embodiment of this invention.
Figure 3:
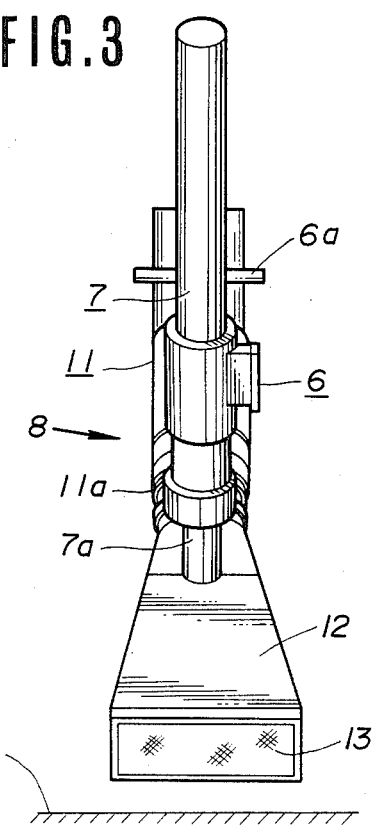
FIG. 3 is a side elevation of the laser surface flaw detecting apparatus of FIG. 2.
Figure 4:
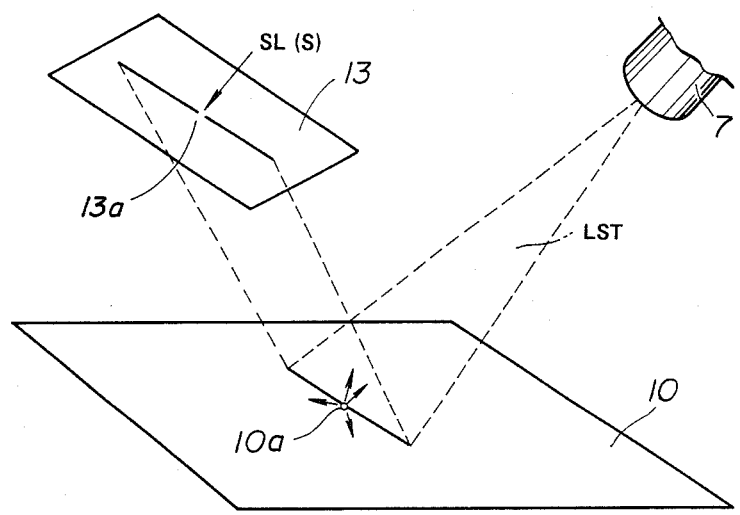
FIG. 4 is a schematic illustration of the operation of a principal part of the laser surface flaw detecting apparatus of FIG. 2.
Figure 5:
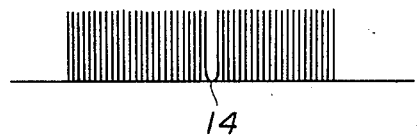
FIG. 5 is a chart of an output of a line sensor.
Figure 6:
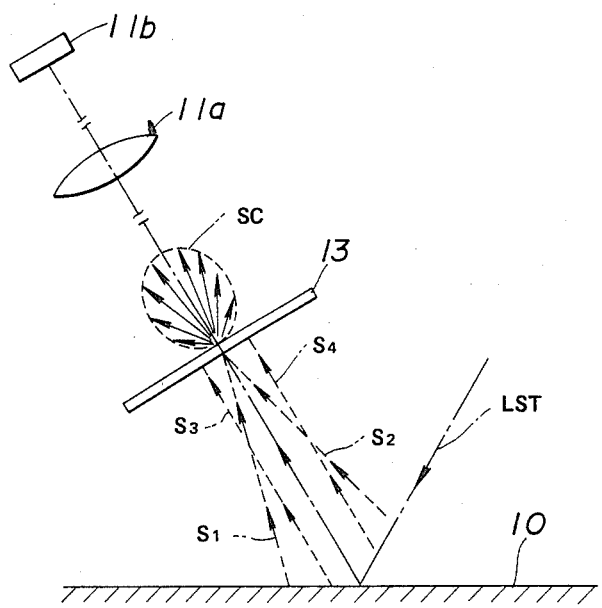
FIG. 6 is a diagram illustrating the operating concepts of the laser surface flaw detecting apparatus of FIG. 2.

The operation of the laser surface flaw detecting apparatus of this embodiment is as follows. As illustrated in FIG. 4, if the inspected surface 10 has any surface flaws 10a, e.g. recesses or small protuberances, the laser light LST from the laser unit 7 incident on the inspected surface 10 will be scattered by the flaw 10a and fall onto the screen 13, thereby projecting onto the screen 13 an expanded slit image SL(S) with a discontinuity at a point 13a corresponding to the flaw 10a. The line sensor 11b, picking up the slit image SL(S) made up of laser light SC scattered by the screen 13 as illustrated in FIG. 6, outputs a train of electrical pulses in which the surface flaw 10a is reflected with a low-level output 14, as illustrated in FIG. 5. The condenser lens 11a requires no focal adjustments relative to the inspected surface 10. The expanded slit image SL(S) projected onto the screen 13 enhances the resolving power of the laser detector unit 8 relative to the surface flaw 10a. Since the line sensor 11b receives the scattered laser beam SC through the condenser lens 11a, the laser detector unit 8 can detect surface flaws 10a in the inspected surface 10 within the capacity of the condenser lens 11a even if the optical paths of reflected laser beam falling onto the screen 13 vary within the range delimited by paths $S_1$ to $S_4$, as shown in FIG. 6, due to changes in the directional relationships among the laser unit 7, the laser detector unit 8 and the inspected surface 10. This moderates the need for accurate adjustment of the optical axes of the laser unit 7 and the laser detector unit 8 relative to the inspected surface 10 and replaces biaxial alignment between the 2-dimensional slit image SL(S) and the line sensor 11b for the prior art triaxial alignment among the inspection point, a laser unit and a laser detector unit.

The laser surface flaw detecting apparatus of this invention moderates the tolerances in inspection conditions as well as specifications of auxiliary equipment for the optical-axis adjustment or alignment. Thus, this apparatus, mounted on a moving apparatus, e.g. a moving industrial robot, facilitates accurate inspection of the inspected surface 10 and can extend its field of application.

SECOND EMBODIMENT

FIGS. 7–12 show a laser surface flaw-detecting apparatus 20 according to a second embodiment of this invention with a control unit omitted from the drawings. The apparatus 20 is attached to a mounting disc 21 at the free end of a movable arm 18 of an industrial robot by means of a matching mounting disc 6a.

The apparatus 20 comprises a body 22 fixed to the mounting disc 6a, an inclination adjuster 23 in the body 22 for both the laser unit 7 and the laser detector unit 8A, a flat support beam 6 fixed to the ends of a pair of brackets 25 in turn movably supported by the body 22, the support beam 6 being pivotable about an axis $\theta_y$ parallel to its longitudinal axis, an axis-rotation adjuster 26 for the laser unit 7 mounted on the backside of the support beam 6 and pivotable in a plane A parallel to the support beam 6, the laser unit 7 mounted at one end of the front surface of the support beam 6 via a movable shaft 7b pivotable about an axis $\theta_x$ perpendicular to the plane A, a laser detector unit 8A fixed to the outer end of the front surface of the support beam 6, and a flaw marker 27 fixed to the center of the lower face of the support beam 6.

Figure 11:
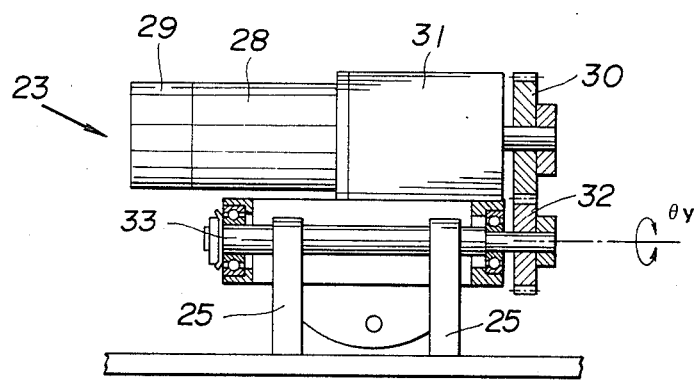
FIG. 11 is an enlarged front view of an inclination adjuster shown in FIG. 7.

The inclination adjuster 23, as shown in FIG. 11, comprises a first electronically controlled motor 28 with a tachogenerator or tachometer 29, a drive spur gear 30 driven by the first motor 28 through a transmission 31, a driven spur gear 32 meshing with the drive spur gear 30 and capable of rotating a shaft 33 journalled in the body 22 about the axis $\theta_y$, the pair of the brackets 25 fixed to the shaft 33, and an electronic control system for the first motor 28, described later. The first motor 28 is capable of adjusting the angular position of the support beam 6. The pivot operation performed by the inclination adjuster 23 will be described later.

Figure 10:
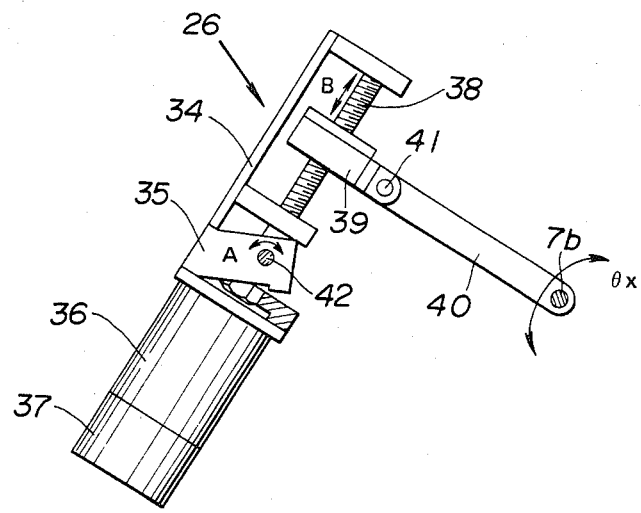
FIG. 10 is an enlarged front view of an axis-rotation adjuster shown in FIG. 7.

The axis-rotation adjuster 26, as shown in FIG. 10, comprises a support frame 34 with a bracket 35, a second electronically controlled motor 36 fixed to a lower end of the support frame 34 and having a tachogenerator or tachometer 37, a ball screw 38 extending the entire length of the support frame 34 and driven by the second motor 36, a nut member 39 driven in the direction of the double-arrow B by the ball screw 38, a pivotable lever 40, one end of which is fixed to the shaft 7b fixed in turn to the laser unit 7 and the other end of which is pivotably connected to the nut member 39 by way of a pivot pin 41. A shaft 42 fixed to the bracket 35 is capable of swinging the support frame 34 in the plane A, as shown in FIG. 10. The second motor 36 is capable of adjusting the position of the lever 40 and therefore the angular position of the shaft 7b and the laser unit 7. The positional adjustment performed by the second motor 36 will also be described later.

Figure 12:
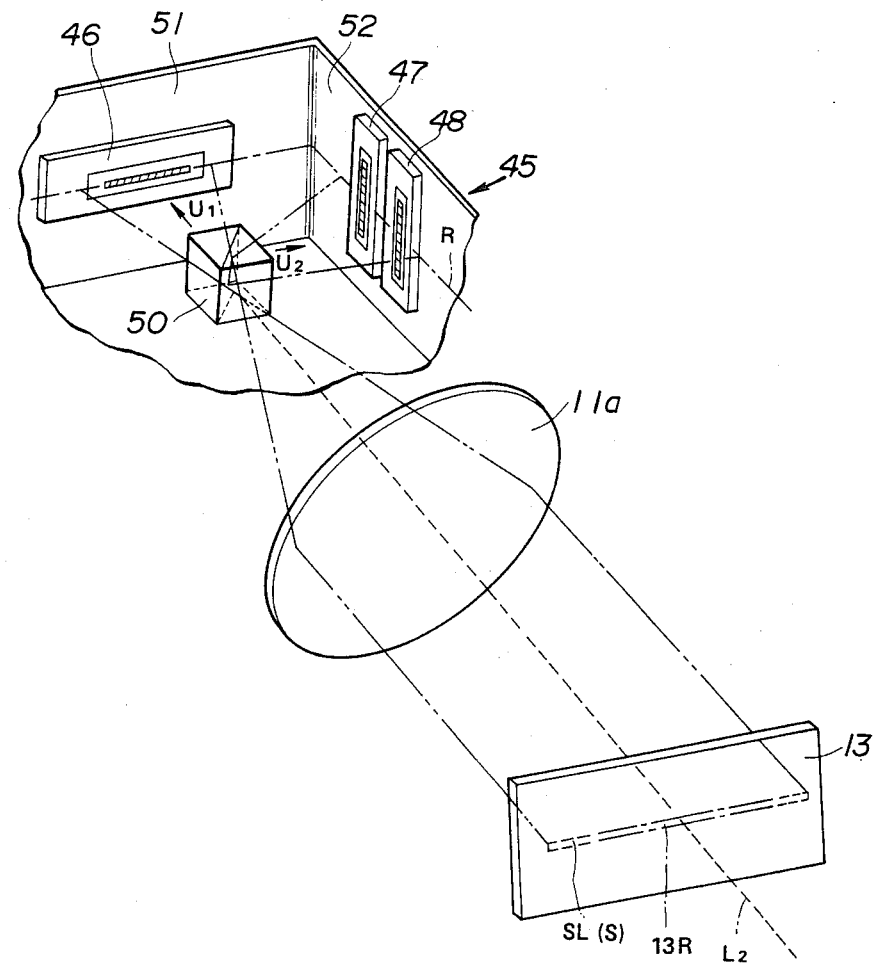
FIG. 12 is a diagram of the interior of a laser detector unit of this invention.

The laser detector unit 8A includes a light-transmissive projecting screen 13, an opaque cylinder 12 and a camera 45. As illustrated in FIG. 12, the camera 45 includes a flaw-detecting line sensor 46 and first and second position-detecting line sensors 47 and 48, the axes of the position detecting line sensors 47 and 48 being, in this case, perpendicular to the axis of the flaw-detecting line sensor 46. The flaw-detecting line sensor 46 continuously monitors a fixed linear reference strip 13R on the screen 13. The first and second position-detecting line sensors 47 and 48 continuously monitor the position of the slit image SL(S) on the screen 13 even if the slit image SL(S) falls outside of the monitored reference strip 13R.

The flaw marker 27 sprays indelible paint near a detected surface flaw so as to mark the surface flaw without interfering with the laser light LS from the laser unit 7 when the laser detector unit 8A detects a recess or small protuberance in the surface, e.g. the painted outer surface 43 of the automotive vehicle door 44, under inspection.

The two positional control operations above-mentioned are described in detail below.

Figure 9:
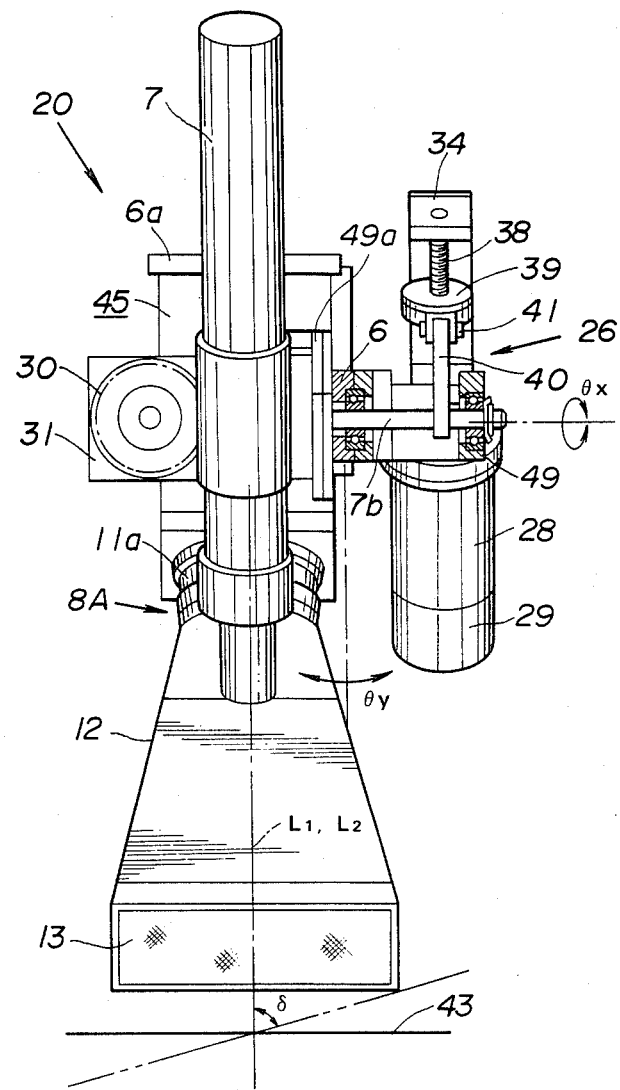
FIG. 9 is a side elevation of the laser surface flaw detecting apparatus of FIG. 7.

As shown in FIGS. 9 and 11, the first motor 28 of the inclination adjuster 23, controlled in accordance with the outputs of the position-detecting line sensors 47 and 48, drives the drive spur gear 30, the driven spur gear 32, the shaft 33 and the pair of the brackets 25 in one direction about the axis $\theta_y$, thereby inclining the support beam 6, i.e. adjusting the inclination $\epsilon$ of the plane defined by the optical axes $L_1$ and $L_2$ to be normal to the painted outer surface 43. That is, the rotational amount of the first motor 28 is controlled so that the plane in which the optical axes $L_1$ and $L_2$ lie is perpendicular to the plane tangent to the point under inspection on the painted outer surface 43. Details of the control of the first motor 28 will be described later.

Figure 8:
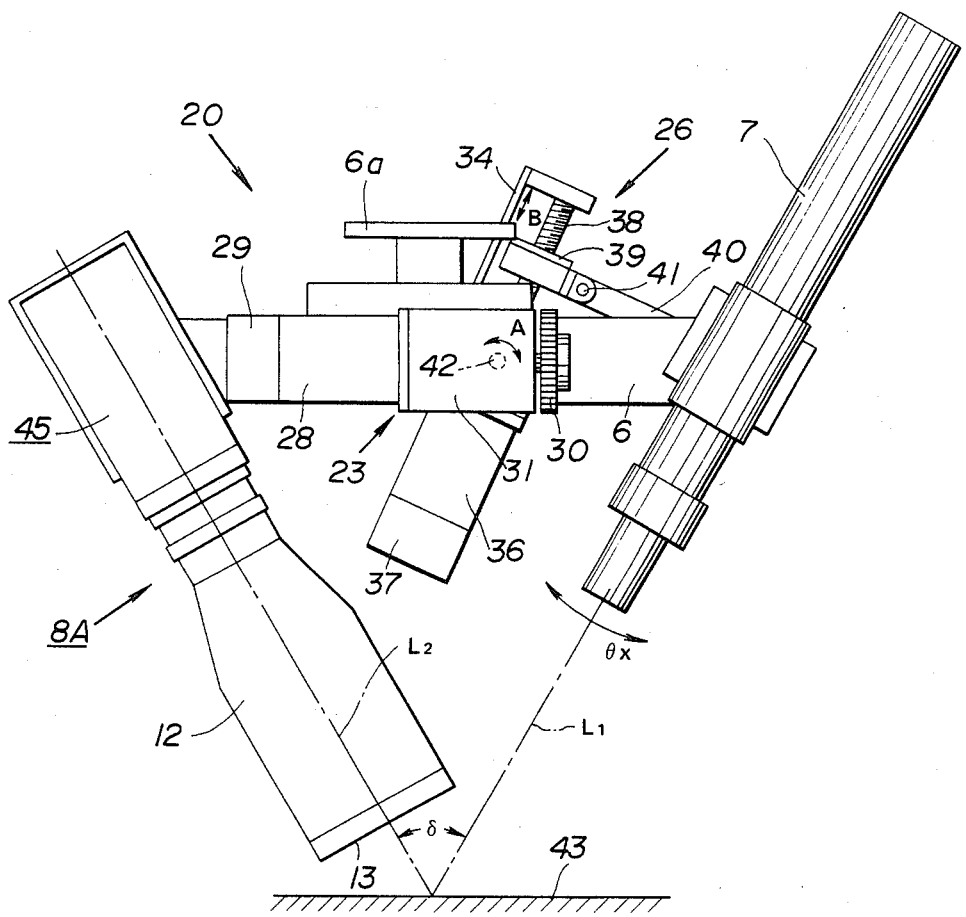
FIG. 8 is a front elevation of the laser surface flaw detecting apparatus of FIG. 7, from which a flaw marker is omitted.

As shown in FIGS. 8 and 10, the second motor 36 of the axis-rotation adjuster 26, controlled in accordance with the outputs of the position-detecting line sensors 47 and 48, drives the ball screw 38, thereby moving the nut member 39 in one direction along the double-arrow B. The nut member 39 concurrently pivots the support frame 34 in one corresponding direction about the shaft 42 and moves the lever 40 and the laser unit 7 in the corresponding direction about the axis $\theta_x$ of the shaft 7b journalled on a pair of brackets 49 fixed to the backsurface of the support beam 6 and fixed to a laser unit holder 49a. That is, the controlled operation of the second motor 36 determines the orientation of the optical axis $L_1$ of the laser unit 7, i.e. the angle of incidence $\delta$. Details of the control of the second motor 36 will be described later.

The detailed internal arrangement of the laser detector unit 8A will be described with reference to FIG. 12. A beam splitter 50 disposed within the camera 45 is capable of dividing scattered laser light from the slit image SL(S) received through the condenser lens 11a approximately evenly between a first split direction $U_1$ and a second split direction $U_2$ perpendicular to the first split direction $U_1$.

The flaw-detecting line sensor 46 lies in the focal plane of the condenser lens 11a and is fixed to a first sensor mount surface 51 normal to the first split direction $U_1$ and behind the beam splitter 50. The flaw-detecting line sensor 46 may consist of 2048 picture elements made up of CCD's or a MOS-PDA, i.e. MOS Photo Diode Array, aligned parallel to the slit image from the beam splitter 50.

The position-detecting line sensors 47 and 48 are mounted in the focal plane of the condenser lens 11a on a second sensor mount surface 52 perpendicular to the first sensor mount surface 51 and to the second split direction $U_2$, disposed to one side (to the right in FIG. 12) of the beam splitter 50. The position-detecting line sensors 47 and 48 may consist of 2048 picture elements made up of CCD's or a MOS-PDA. The position-detecting line sensors 47 and 48 may be arranged parallel to each other. The axes of the position-detecting line sensors 47 and 48 are oblique to, or in the second embodiment, perpendicular to the slit image projected in direction $U_2$ by the beam splitter 50. The position-detecting line sensors 47 and 48 monitor the position and orientation of the slit image relative to the flaw-detecting line sensor 46. The optical axis $L_2$ of the laser detector unit 8A is common to the condenser lens 11a and passes through the center of the flaw-detecting line sensor 46.

When the slit image $SL_2(F)$ lies in the same plane as the photosensitive element of the flaw-detecting line sensors 46, the split slit image $SL_2(P)$ falls on the central picture element (1024th) of the position-detecting sensor 47 and 48.

The spacing between the position-detecting line sensors 47 and and 48 is chosen in correspondance to the maximum expected curvature of the painted outer surface 43 of the automotive vehicle door 44 so that the slit image $SL_2(P)$ will impinge on both position-detecting line sensors 47 and 48 regardless of its curvature or orientation; the greater the maximum expected curvature, the smaller the spacing.

The operation of the above-described laser detector unit 8A will be described in detail below.

As previously described, when the slit image SL(S) is formed within the monitored reference strip 13R, the flaw-detecting line sensor 46 can detect the presence of flaws 13a, as shown in FIG. 4.

Figure 13:
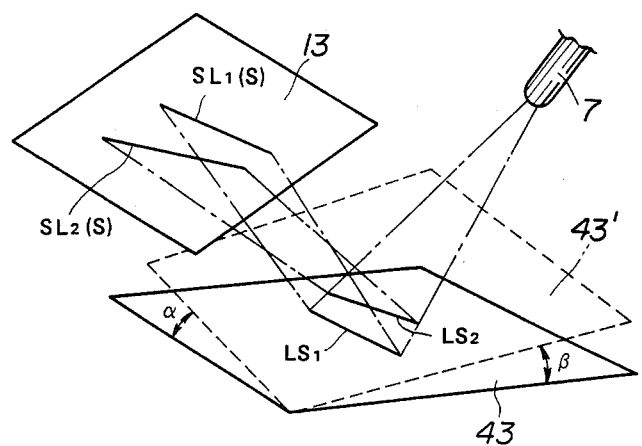
FIG. 13 is a diagram of the 2-dimensional displacement of a slit image on a scattering screen effected by 3-dimensional displacement of a painted outer surface.

As shown in FIG. 13, when the laser unit 7 transmits a laser slit beam $LS_1$ onto the painted outer surface 43 indicated by the solid lines, a corresponding slit image $SL_1(S)$ is formed within the monitored reference strip. If the laser unit 7 transmits a laser slit beam $LS_2$ onto the painted outer surface 43 indicated by the broken lines, which is 3-dimensionally angularly displaced from the original position of the painted outer surface 43 through angles $\alpha$ and $\beta$, the slit image $SL_2(S)$ will be 2-dimensionally displaced from the original slit image $SL_1(S)$.

This 2-dimensional displacement of the slit image $SL_2(S)$ with respect to the slit image $SL_1(S)$ consists of a translational offset perpendicular to the length of the slit image $SL_1(S)$ and an angular displacement with respect to the slit image $SL_1(S)$.

In this case, any changes in the length of the slit image accompanying the 2-dimensional displacement can be ignored.

Figure 14:
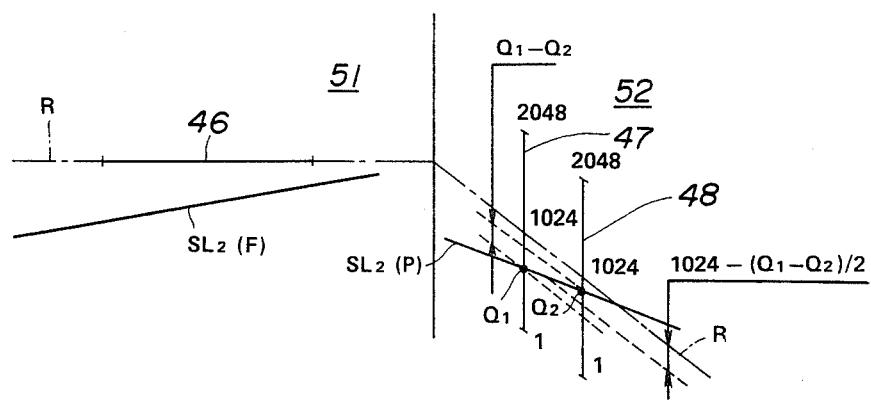
FIG. 14 is a diagram showing how position detection of the slit image is performed by position detecting line sensors.

As shown in FIG. 14, the respective position detecting line sensors 47 and 48 detect intersection image-forming points $Q_1$ and $Q_2$ onto which the slit image $SL_2(P)$ transmitted in the second split direction $U_2$ falls, thereby detecting the deviation (i.e. position) of the slit image $SL_2(S)$ from the monitored reference strip 13R.

Figure 15A:
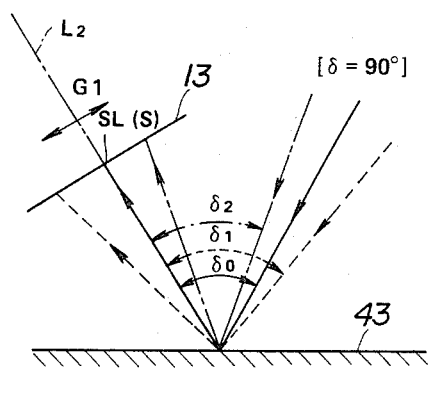
FIG. 15A is a diagram of parallel 2-dimensional displacements of the slit image when an inclination $\epsilon$ is fixed as axis rotation $\delta$ varies.

As shown in FIG. 15A, when the axis-rotation adjuster 26 changes an original angle $\delta_0$ to an angle $\delta_1$ or $\delta_2$ while holding the inclination $\epsilon$ between the optical plane and surface 43 at 90°, the slit image SL(S) is displaced in a direction of the double-arrow G1 perpendicular to the major axis of the monitored reference strip 13R to an extent determined by the angular deviation $\delta_0 - \delta$.

Figure 15B:
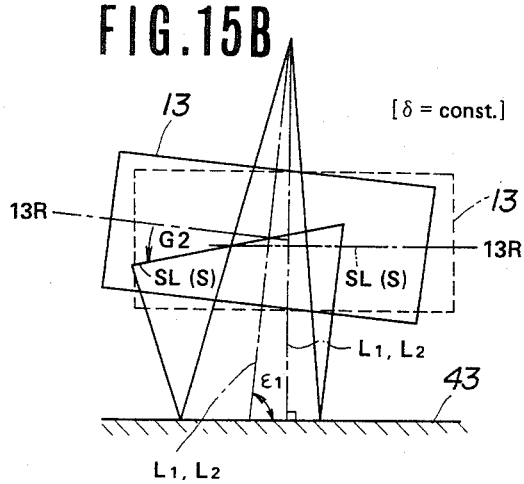
FIG. 15B is a diagram of the angular 2-dimensional displacements of the slit image when the axis rotation $\delta$ is fixed as the inclination $\epsilon$ varies.

As shown in FIG. 15B, when the inclination adjuster 23 changes the inclination $\epsilon$ from 90° to an angle $\epsilon 1$ while holding the axis-rotation angle $\delta$ fixed, the axis of the slit image SL(S) shown in phantom line on the screen 13 shown in broken line, depending on the change in the inclination $\epsilon$, shifts angularly from the monitored reference strip 13R shown in solid line on the screen 13 shown in solid line.

In summary, when changes in the spatial relationships among the laser unit 7, the laser detector unit 8A and the painted outer surface 43 effect the position and/or orientation of the slit image SL(S) relative to the monitored reference strip 13R, the rotational and translational displacements serve as exact indices for the required extent of operation of the first motor 28 of the inclination adjuster 23 and the second motor 36 of the axis-rotation adjuster 26 respectively, thus adjusting the inclination $\epsilon$ and the angle of incidence $\delta/2$ so as to return the displaced slit image SL(S) to the monitored reference strip 13R.

As illustrated in FIG. 14, the expressions $\{1024-(Q_1+Q_2)/2\}$ and $(Q_1-Q_2)$ respectively represent the translational and rotational displacements of the slit image $SL_2(S)$ from the monitored reference strip 13R. Evaluating the expression $\{1024-(Q_1+Q_2)/2\}$ yields the desired orientation about axis $\theta_x$ of the laser unit 7, and the amount and direction of rotation of the second motor 36 of the axis-rotation adjuster 26, needed to produced the required change $\Delta\delta$. Evaluating the expression $(Q_1-Q_2)$ determines the desired orientation of the support beam 6 and the amount and direction of movement of the first motor 28 or the inclination adjuster 23 needed to produced the required change $\Delta\epsilon$. These two adjustments can return the displaced slit image SL(S) to coincidence with monitored reference strip 13R.

Figure 16:
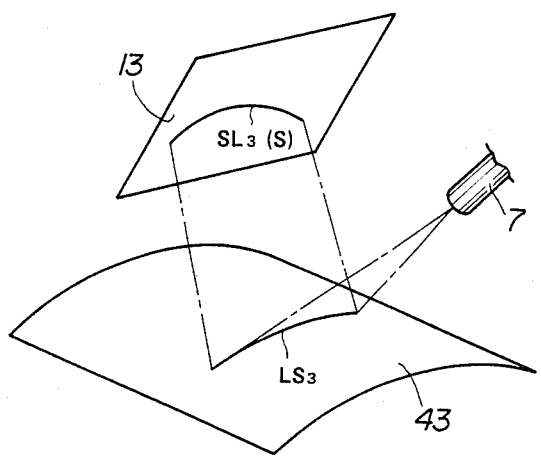
FIG. 16 is a diagram showing how a curved slit image of a curved painted outer surface under inspection is formed on the screen.
Figure 17:
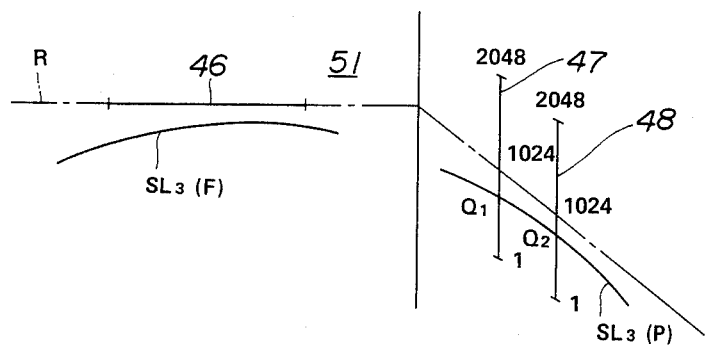
FIG. 17 is a diagram showing how the position of the curved slit image shown in FIG. 16 is detected by position detecting line sensors.

If the laser unit 7 projects a laser slit beam $LS_3$ onto a curved painted outer surface 43, the slit image $SL_3(S)$ will also be curved as shown in FIG. 16 so as to intersect the position-detecting line sensors 47 and 48 at the intersection image-forming points $Q_1$ and $Q_2$. As previously described, the inclination adjuster 23 and the axis-rotation adjuster 26, in accordance with the values of the expressions $\{1024-(Q_1+Q_2/2\}$ and $(Q_1-Q_2)$ shown in FIG. 17, return the curved slit image $SL_3(S)$ to the straight monitored reference strip 13R with the points of the curve coincident with the points $Q_1$, $Q_2$ being centered on the flaw detecting line sensor 40, as shown in FIG. 18.

The control system for the surface flaw detecting apparatus 20 will be described in detail with reference to FIGS. 19 to 23. In this control system, a first sensor drive circuit 53, which drives the first position-detecting line sensor 47 in response to a monitor instruction signal SA from a position control unit 55 of a control section 56, receives a train of first video signals outputted from the first position-detecting line sensor 47. The first sensor drive circuit 53 samples the outputs of all the sensor pixels and sends the position control unit 55 the address corresponding to the intersection image-forming point $Q_1$ shown in FIG. 25, i.e. the pixel receiving the greatest intensity.

In more detail, the first sensor drive circuit 53 recognizes the greatest pixel intensity in a single sample frame by using the analog intensity levels as a floating binary reference system, thus outputting a single binary signal pulse $Q_1$ representing the detected intersection image-forming point $Q_1$, as shown in FIG. 20(A). The first sensor drive circuit 53 detects the leading or trailing edge of the video signal pulse $Q_1$, or the average of the leading and trailing edges of the video signal pulse $Q_1$ and outputs the corresponding address value $Q_1$.

A second sensor drive circuit 54 drives the second position-detecting line sensor 48 and outputs a address value $Q_2$ shown in FIG. 21(B), similarly to the first sensor drive circuit 53.

A third sensor drive circuit 57, which drives the flaw-detecting sensor 46 while in the presence of a monitor instruction signal SB from a flaw-detection control unit 58 of the control section 56, receives a train of third video signals from the flaw-detecting line sensor 46. The third sensor drive circuit 57 processes the pixel outputs of the flaw-detecting line sensor 46 and sends the flaw-detection control unit 58 a flaw-evaluation signal W (if there is no flaw, the signal value W is 0) as shown in FIG. 20(C).

The third drive circuit 57 employs the same floating binary system used in the first drive circuit 53 to output a single binary video signal pulse W indicating a detected surface flaw, if any, in an inspection strip area 43 on the painted outer surface 43. The third sensor drive circuit 53 responds to the trailing edge and the width of the video signal pulse W and outputs the flaw-evaluation signal in accordance with the dimensions of the surface flaw.

As shown in FIG. 19, a servo-amplifier 59 receives as a plus or minus voltage-adjustment signal $V_x$ derived by a D-A converter 60 from an axis-rotation-adjustment value $D_x$ generated by the position control unit 55. The axis-rotation-adjustment value $D_x$ represents the desired angular correction (a vector quantity) of the laser unit 7 about its axis $\theta_x$. The servo-amplifier 59 also receives a velocity feedback signal from the tachogenerator 37 and drives the second motor 36 of the axis-rotation adjuster 26.

Similarly, a servo-amplifier 61 receives a plus or minus voltage-adjustment signal $V_y$ derived by a D-A converter 62 from an inclination-adjustment value $D_y$ generated by the position control unit 55. The inclination-adjustment value $D_y$ represents the desired angular correction (a vector quantity) of the support beam 6 about its axis $\theta_y$. The servo-amplifier 61 also receives a velocity feedback signal from the tachogenerator 29 and drives the first motor 28 of the inclination adjuster 23.

A power circuit 63, in response to a laser excitation instruction signal SL from the position control unit 55, energizes the laser unit 7.

A marker driver 64, in response to a marker instruction signal SM from the flaw detection control unit 58, drives an electromagnetic valve 65 to supply a spring-loaded working cylinder 27a of the flaw market 27 with compressed air. Thus, the flaw marker 27 ejects atomized paint onto the painted outer surface 43.

As shown in FIG. 19, the control unit 56 comprises the position control unit 55, the flaw detection control unit 58, and the D-A converters 60 and 62.

The position control unit 55 may be a microprocessor and receives and sequentially processes the address values $Q_1$ and $Q_2$, a start instruction signal SS, a stop-instruction signal ST and a pause instruction signal SE and outputs the monitor instruction signal SA, the laser excitation instruction signal SL, a robot-operating instruction signal SR, the axis-rotation-adjustment value $D_x$, the inclination-adjustment value $D_y$ and a flaw-detection enable signal SOK in accordance with a program described below with reference to FIGS. 21 and 22.

When the robot arm 18 reaches a pre-programmed point matching a flaw-detection start point $F_0$ over the painted outer surface 43, the start instruction signal SS is outputted. When the robot arm 18 reaches another pre-programmed point matching a flaw-detection finish point $F_n$ over the painted outer surface 43, the stop instruction ST is outputted. As the robot arm 18 follows an inspection path across the painted outer surface 43, at each turning or return-scan point, on such as between points $F_m$ and $F_{m+1}$ in FIG. 7, the pause instruction signal SE is outputted.

Similarly, the flaw-detection control unit 58 may be a microprocessor and receives and sequentially processes the flaw evaluation signal W, an inspection start instruction signal SSS and an inspection stop instruction signal SST from a robot control panel (not shown), a flaw-detection reference value signal l from a controller (not shown) of the surface-flaw-detecting apparatus 20, and the flaw detection enable signal SOK and outputs the monitor instruction signal SB and the marker instruction signal SM, in accordance with a program described below with reference to FIG. 23.

The robot control section outputs the inspection start instruction signal SSS and the inspection stop instruction signal SST at the same timing of the starting instruction signal SS and the stop instruction signal ST.

The operation of the position control unit 55 and the flaw-detection control unit 58 will be described with reference to FIGS. 21 to 23.

Figure 7:
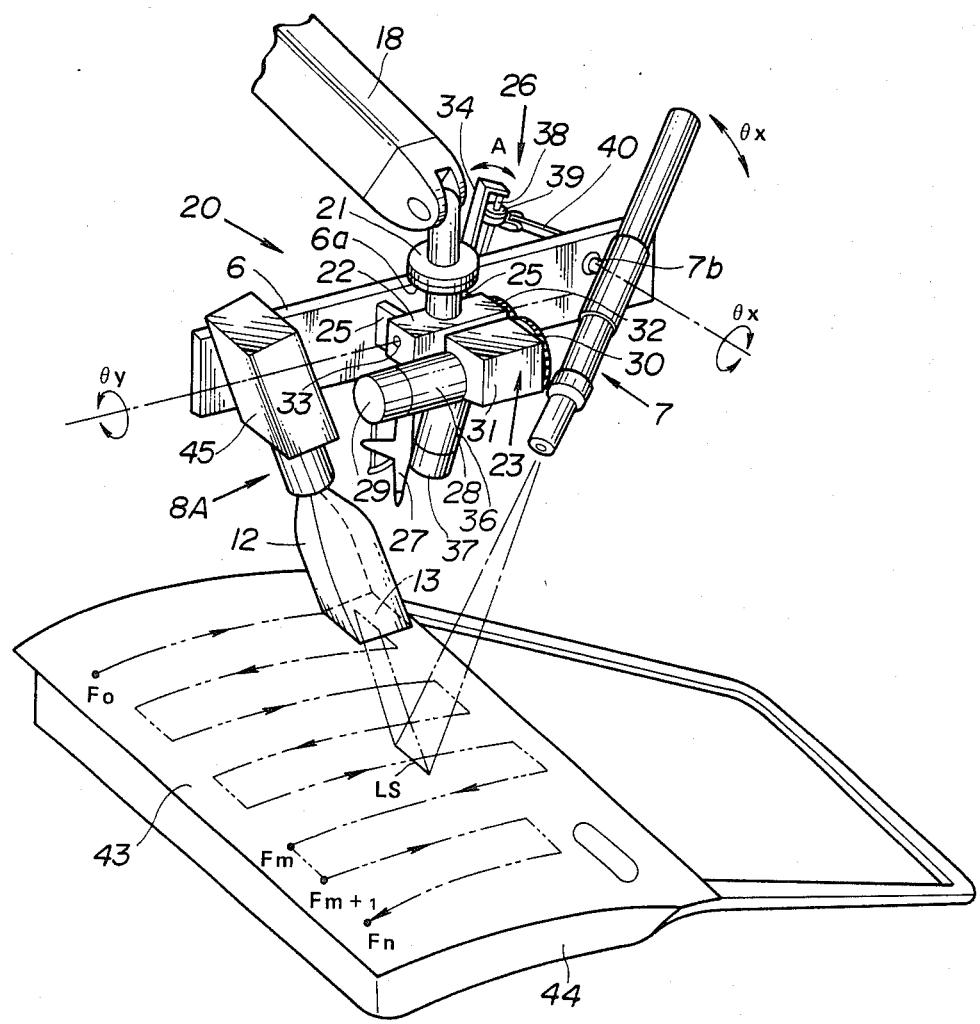
FIG. 7 is a perspective view of a laser surface flaw detecting apparatus according to a second embodiment of this invention, from which view a control system is omitted.

Suppose that the robot of FIG. 7 follows the path drawn in double-dot-and-dash lines from the flaw-detection start point $F_0$ to the flaw-detection finish point $F_n$.

As shown in FIG. 21, at STEP 1, a CPU (not shown) of the position control unit 55 checks for a reception of the start instruction signal SS from the robot control panel and, upon confirmation of reception of the start instruction signal SS, advances to STEP 2. In other words, the position control unit 55 cannot advance to STEP 2 until it receives the start instruction signal SS.

At STEP 2, the position control unit 55 sends the first and second sensor drive circuits 53 and 54 the monitor instruction signal SA and the power circuit 63 the laser-excitation instruction signal SL. Thus, the laser unit 7 transmits the laser slit beam LS onto the painted outer surface 43 and the first and second sensor drive circuits 53 and 54 drive the respective position-detecting line sensors 47 and 48 to output the address values $Q_1$ and $Q_2$.

At STEP 3, the position control unit 55 executes a subroutine consisting of STEPS 4 to 9 shown in FIG. 22. At STEP 4, the position control unit 55 receives the latest address values $Q_1$ and $Q_2$. At STEP 5, the position control unit 55 evaluates the translational displacement expression $\{1024-(Q_1+Q_2)/2\}$ to derive the axis-rotation-adjustment value $D_x$. At STEP 6, the position control unit 55 evaluates the angular displacement expression $(Q_1-Q_2)$ to derive the inclination-adjustment value $D_y$. When the slit image SL(S) coincides with the monitored reference strip 13R, the address values $Q_1$ and $Q_2$ are both 1024, and the axis-rotation-adjustment value $D_x$ and the inclination-adjustement value $D_y$ are both 0. At STEP 7, the position control unit 55 concurrently sends the axis-rotation-adjustment value $D_x$ and the inclination-adjustment value $D_y$ to the respective D-A converters 60 and 62. At STEP 8, the position control unit 55 receives new address value $Q_1$ and $Q_2$. At STEP 9, the position control unit 55 checks whether or not the new address values $Q_1$ and $Q_2$ both equal 1024. If both the new address values $Q_1$ and $Q_2$ are 1024, the position control unit 55 ends the subroutine and advances to STEP 10 of the main program. On the other hand, if the new address values $Q_1$ and $Q_2$ are not both equal to 1024, the subroutine returns to STEP 4. STEPS 1 to 9 initialize the surface-flaw-detecting apparatus 20 after the robot arm 18 has reached the flaw-detection start point $F_0$.

At STEP 10, the position control unit 55 sends the robot control section the robot-operation instruction signal SR so that the robot can start tracking the pre-programmed surface scan. At STEP 11, the position control unit 55 repeats the subroutine shown in FIG. 22.

At STEP 12, the position control unit 55 checks for receipt of the pause-instruction signal SE from the robot control section and advances to STEP 13 in the absence of the pause-instruction signal SE. On the other hand, the control unit 55, upon receipt of the pause-instruction signal SE, returns to STEP 11 and repeats the subroutine of FIG. 22.

At STEP 13, the position control unit 55 outputs the flaw-detection enable signal SOK to the fault-detection unit 58 to enable use of the flaw-detecting line sensor 46. Thus, STEP 12 has the effect of temporarily disabling surface flaw recognition while allowing laser slit image positioning by the positioning line sensors 47, 48 when the robot arm reaches the end of each leg of the surface scan path across the inspected surface.

At STEP 14, the position control unit 55 checks for receipt of the stop instruction signal ST from the robot control unit. Upon receipt of the stop instruction signal ST, the position control unit 55 advances to STEP 15. The control unit 55 returns to STEP 11 in the absence of the stop instruction signal ST.

At STEP 15, the position control unit 55 stops outputting the monitor instruction signal SA and the laser-excitation instruction signal SL and ends the program.

The effect of the control program shown in FIGS. 21 and 22 is that the image of the laser slit beam LS reflected by the painted outer surface 43 will be held continuously within the monitored reference strip on the screen 13 even as the relationships between the laser unit 7, the laser detector unit 8A and the painted outer surface 43 change due to various factors such as the curvature of the painted outer surface 43, so that the inventive surface-flaw-detecting apparatus 20 is applicable to various kinds of reflective surfaces.

As shown in FIG. 23, at STEP 16, a CPU (not shown) of the flaw detecting control unti 58 checks for receipt of the inspection start instruction signal SSS and upon receipt advances to STEP 17. In other word, the flaw detecting control unit 58 simply waits for the reception of the inspection start instruction signal SSS.

At STEP 17, the flaw detecting control unti 58 sends the third sensor drive circuit 46 the monitor instruction signal SB to enable transmission of the flaw-evaluation signal W.

At STEP 18, the flaw-detecting control unit 58 waits for the flaw-detection enable signal SOK from the position control unit 55. Upon receipt of this signal SOK, the flaw-detecting control unit 58 advances to STEP 19.

At STEP 19, the flaw-detecting control unit 58 receives the flaw-evaluation signal W from the third sensor drive circuit 46.

At STEP 20, the flaw-detecting control unit 58 compares the flaw evaluation signal value W with the flaw reference value 1. The flaw-detecting control unit 58, advances to STEP 21 when $W \geq 1$ and on the other hand, returns to STEP 18 when $W < 1$.

At STEP 21, the flaw-detecting control unit 58 sends the marker instruction signal SM to the marker driver 64. Thus, the flaw marker 27 marks the position of the surface flaw.

At STEP 22, the flaw-detecting control unit 58 checks for receipt of the inspection stop instruction signal SST from the robot control section. The flaw-detecting control unit 58, advances to STEP 23 upon receipt of the signal SST and on the other hand, in the absence of the inspection stop instruction signal SST, returns to STEP 18.

At STEP 23, the flaw detecting control unit 58 stops outputting the monitor instruction signal SB and ends the program of FIG. 23.

THIRD EMBODIMENT

FIGS. 24 and 25 illustrate an arrangement of a flaw-detecting sensor 46 and position-detecting sensors 47 and 48 according to a third embodiment of this invention. The position detecting sensors 47 and 48 are disposed to either side of the flaw detecting sensor 46 and are aligned perpendicular to the flaw detecting sensor 46. The reference axis R of the flaw detecting sensor 46 crosses the central picture elements, i.e. 1024th picture elements of the position detecting sensors 47 and 48. As shown in FIG. 25, the expression $\{1024-(Q_1+Q_2)/2\}$ represents the translational displacement of the slit image $SL_3(S)$ from the monitored reference strip and the expression $(Q_1-Q_2)$ represents the angular displacement of the slit image $SL_3(S)$ from the monitored reference strip, as in the second embodiment. The third embodiment obviates the need for the beam splitter.

Another embodiment of this invention may employ a reflective but scattering screen in place of the scattering, transmissive screen 13. Still another embodiment may employ a laser spot beam. Still another embodiment may employ an area sensor instead of the line sensor regardless of the type of laser beam used in order to further moderate the requirements for accurately controlled inspection conditions.

In another embodiment, the surface flaw detecting apparatus is fixed and the automotive vehicle door 44 is movable.

In another embodiment, the optical axis of the laser detector unit is movable in order to adjust the axis-rotation offset $\delta$ and the optical axis of the laser unit is fixed. Alternatively, both optical axes may be adjustable.

In another embodiment, a device mounted pivotably on the shaft 7b comprises only a lens system used to convert the laser beam to a laser slit. The laser beam is conducted to the lens system through an optical fiber, so that a more compact surface-flaw-detecting apparatus can be obtained.

This invention is applicable to surfaces of a vehicle body which have been painted, or to various specular surfaces.

In addition, the inclination adjuster and the axis-rotation adjuster are not limited to the structures shown in the drawings. Any devices capable of adjusting the inclination $\epsilon$ and the angular axis offset $\delta$ would serve.

What is claimed is:

1. A method for detecting flaws in the surface of an object to be inspected, comprising the steps of:
    transmitting a laser beam in a slit configuration onto a surface of the object;
    projecting the laser beam reflected by the surface of the object onto a part of a light-scattering plane sceen;
    forming an image of the surface of the object on the part of the screen, the image having a first configuration in the form of a continuous slit when the surface of the object has no flaw and having a second configuration in the form of a slit with a corresponding discontinuity when the surface of the object has a flaw;

detecting both the first and second configurations of the image of the surface on said part of said screen; and producing a train of pulses in response to said first and second configurations of the image in which a possible surface flaw is indicated by a particular output level.

2. An apparatus for detecting surface flaws, comprising:

means for transmitting a laser slit beam onto a specular surface of an object to be inspected;

a light-scattering screen onto which the laser slit beam is reflected by the surface so as to form an image of the surface on the screen;

a flaw-detecting means for detecting the image of the surface at a predetermined portion of the screen;

means for detecting the position of the image of the surface relative to the predetermined portion of the screen;

means for adjusting the angle subtended by the optical axes of said laser slit beam transmitting means and of the flaw detecting means in accordance with the output of said position detecting means; and means for adjusting the inclination of the plane defined by the optical axes of said laser slit beam transmitting means and the flaw-detecting means relative to the surface in accordance with the output of said position detecting means.

3. An apparatus as recited in claim 2, wherein said flaw-detecting means comprises a flaw-detecting line sensor capable of monitoring a reference strip of the screen and said position detecting means comprises two position-detecting line sensors, the axis of the flaw-detecting line sensor lying oblique to the axes of the position-detecting line sensors.

4. An apparatus as recited in claim 3, wherein the position-detecting line sensor are disposed in the same plane as the flaw-detecting line sensor and at opposite ends of the flaw-detecting line sensor.

5. An apparatus as recited in claim 3, further comprising:

a beam splitter splitting the scattered laser beam transmitted from the screen into two different directions, a first split laser beam being directed onto the flaw-detecting line sensor and a second split laser beam being directed onto the position-detecting line sensors.

6. An apparatus as recited in claim 5, wherein the position-detecting line sensors lie in a plane oblique to the plane of the flaw detecting line sensor and wherein the spacing between the position-detecting line sensors is determined by the maximum curvature of the surface.

7. An apparatus as recited in claim 2, wherein said screen is substantially 2-dimensional.

8. An apparatus as recited in claim 2, wherein said screen is made of a light-transmissive material.

9. An apparatus as recited in claim 4, wherein both the position-detecting line sensors consist of a plurality of picture elements each converting an incident light intensity to a corresponding electrical signal, the axis of the flaw-detecting line sensor lying in a plane including the central picture elements of both position-detecting line sensors and wherein said angle adjusting means determines the axes-angle based on the average distance of the image from the central picture elements and said inclination adjusting means determines the inclination based on the average slope of the image relative to the flaw-detecting line sensor.

10. An apparatus as recited in claim 9, further comprising:

a first sensor drive circuit means for sampling outputs of all of the picture elements of a first position-detecting line sensor, identifying the pixel with the most intense incident light and outputting a corresponding address value representing the location of a first point of the image;

a second sensor drive circuit means for sampling the outputs of all of the picture elements of the other position-detecting line sensor, identifying the pixel with the most intense incident light and outputting a corresponding address value representing a second point of the image; and a position control means consisting of a microprocessor responsive to said address values representing the locations of said first and second image points for deriving said average distance and average slope values.

11. An apparatus as recited in claim 4, wherein the flaw detecting means is disposed in a fixed spatial relationship with the screen, and the position detecting means is disposed in a fixed spatial relationship with the screen.

* * * * *